United States Patent
Hoffmann et al.

(10) Patent No.: US 8,937,155 B2
(45) Date of Patent: Jan. 20, 2015

(54) **ANTIMICROBIAL PEPTIDES AND PEPTIDE DERIVATIVES DERIVED FROM *ONCOPELTUS FASCIATUS***

(75) Inventors: Ralf Hoffmann, Grossposna (DE); Daniel Knappe, Leipzig (DE)

(73) Assignee: AMP Therapeutics GmbH, Leipzig (DE)

( * ) Notice: Subject to any disclaimer, the term of this patent is extended or adjusted under 35 U.S.C. 154(b) by 0 days.

(21) Appl. No.: 13/698,783

(22) PCT Filed: May 27, 2011

(86) PCT No.: PCT/EP2011/058721
§ 371 (c)(1),
(2), (4) Date: Jan. 28, 2013

(87) PCT Pub. No.: WO2011/147960
PCT Pub. Date: Dec. 1, 2011

(65) Prior Publication Data
US 2013/0130994 A1    May 23, 2013

(30) Foreign Application Priority Data
May 28, 2010  (EP) .................................... 10164251

(51) Int. Cl.
| A61K 38/00 | (2006.01) |
| C07K 7/08 | (2006.01) |
| C07K 2/00 | (2006.01) |
| C07K 14/00 | (2006.01) |
| C07K 14/435 | (2006.01) |
| C12Q 1/18 | (2006.01) |

(52) U.S. Cl.
CPC ............. *C07K 7/08* (2013.01); *C07K 14/43563* (2013.01); *C12Q 1/18* (2013.01); *A61K 38/00* (2013.01)
USPC ............................ 530/326; 514/2.3; 514/21.4

(58) Field of Classification Search
CPC .... A61K 38/00; C07K 7/08; C07K 14/43563; C12Q 1/18
See application file for complete search history.

(56) References Cited

FOREIGN PATENT DOCUMENTS

WO    WO 2010/086401    8/2010

OTHER PUBLICATIONS

Definition of Derivative, from http://cancerweb.ncl.ac.uk/cgi-bin/omd?query=derivative, pp. 1-5, accessed Jul. 7, 2005.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Alphabetical List of Diseases, from http://www.mayoclinic.org/diseases-treatments/alphalist-all.html, pp. 1-26, accessed Oct. 10, 2013.*
Overview of Fungal Infection-Merck Manual, pp. 1-2, accessed Oct. 10, 2013.*
Knappe, et al., "Oncocin (VDKPPYLPRPRPPRRIYNR-NH2): A Novel Antibacterial Peptide Optimized againts Gram-Negative Human Pathogens", Journal of Medicinal Chemistry, vol. 53, No. 14, Jul. 2010, pp. 5240-5247.
Knappe, et al., "Chemical modifications of short antimicrobial peptides from insects and vertebrates to fight multi-drug resistant bacteria", Advances in Experimental Medicine and Biology, vol. 611, Jan. 1, 209, pp. 395-396.
Li, et al., "Apidaecin-type peptides: Biodiversity, strucuture-function relationships and mode of action", Peptides, vol. 27, No. 9, Sep. 1, 2006, pp. 2350-2359.

* cited by examiner

*Primary Examiner* — Julie Ha
*Assistant Examiner* — Li Ni Komatsu
(74) *Attorney, Agent, or Firm* — Panelli Haag & Kilger PLLC

(57) ABSTRACT

The present invention relates to a antimicrobial peptide or peptide derivative comprising the following sequence: $Sub_1$-$X_1$-$D_2$-$K_3$-$P_4$-$P_5$-$Y_6$-$L_7$-$P_8$-$R_9$-$P_{10}$-$X_2$-$P_{12}$-$P_{13}$-$R_{14}$-$X_3$-$T_{16}$-$P_{17}$-$N_{18}$-$N_{19}$-$X_4$-$Sub_2$. The invention further relates to multimers comprising said peptides or peptide derivatives. Moreover, the invention provides a peptide or peptide derivative for use in the treatment of a disease. The peptide or peptide derivative may also be used in the screening for novel antimicrobial compounds.

14 Claims, 1 Drawing Sheet

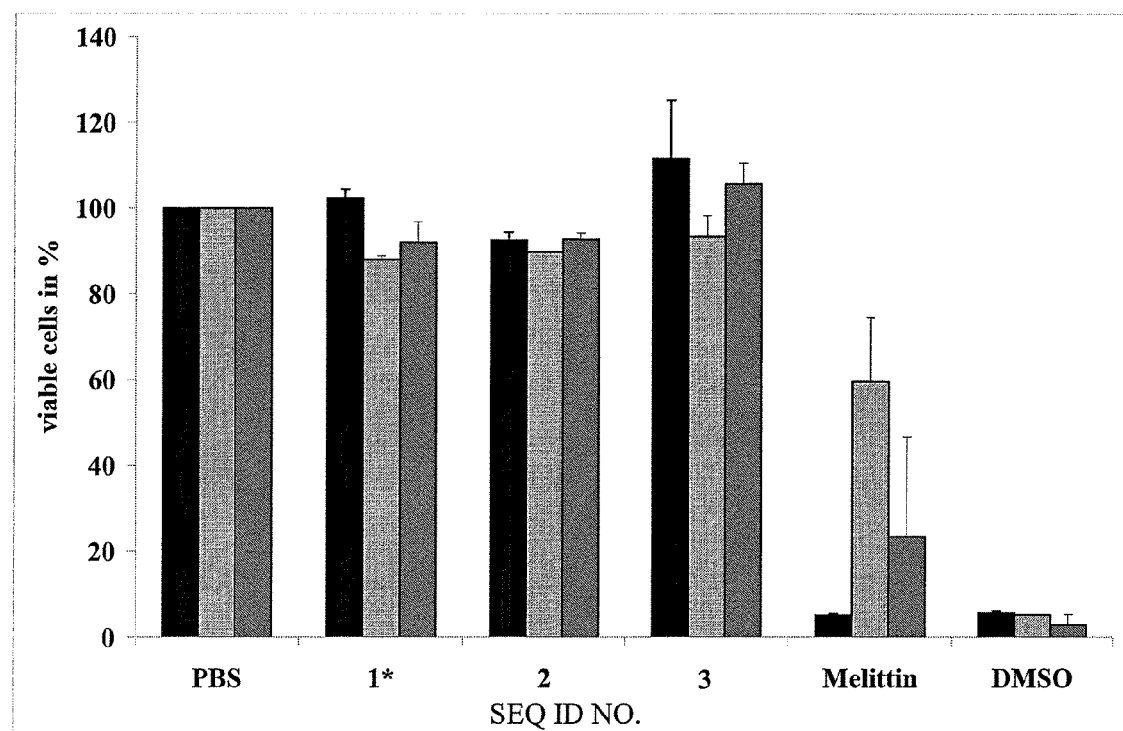

SEQUENCE LISTING

```
<160> NUMBER OF SEQ ID NOS: 11

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Arg-NH2

<400> SEQUENCE: 1

Val Asp Lys Pro Pro Tyr Leu Pro Arg Pro Arg Pro Pro Arg Arg Ile
1               5                   10                  15

Tyr Asn Arg

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (15)..(15)
<223> OTHER INFORMATION: Orn
<220> FEATURE:
<221> NAME/KEY: MOD_RES
<222> LOCATION: (19)..(19)
<223> OTHER INFORMATION: Orn-NH2

<400> SEQUENCE: 2

Val Asp Lys Pro Pro Tyr Leu Pro Arg Pro Arg Pro Pro Arg Xaa Thr
1               5                   10                  15

Tyr Asn Xaa

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 4tHyp
<220> FEATURE:
<221> NAME/KEY: MOD_RES
<222> LOCATION: (15)..(15)
<223> OTHER INFORMATION: 4tHyp
<220> FEATURE:
<221> NAME/KEY: MOD_RES
<222> LOCATION: (19)..(19)
<223> OTHER INFORMATION: Orn-NH2

<400> SEQUENCE: 3

Val Asp Lys Pro Pro Tyr Leu Pro Arg Pro Arg Pro Xaa Arg Xaa Thr
1               5                   10                  15

Tyr Asn Xaa

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Orn
<220> FEATURE:
<221> NAME/KEY: MOD_RES
<222> LOCATION: (19)..(19)
<223> OTHER INFORMATION: Orn-NH2

<400> SEQUENCE: 4

Val Asp Lys Pro Pro Tyr Leu Pro Arg Pro Arg Pro Arg Xaa Ile
1               5                   10                  15

Tyr Asn Xaa

<210> SEQ ID NO 5
<211> LENGTH: 20
<212> TYPE: PRT
<213> ORGANISM: Oncopeltus fasciatus
<220> FEATURE:
<221> NAME/KEY: MOD_RES
<222> LOCATION: (11)..(11)
<223> OTHER INFORMATION: This position can be Pro or any naturally
      occurring amino acid
```

<400> SEQUENCE: 5

Val Asp Lys Pro Pro Tyr Leu Pro Arg Pro Xaa Pro Pro Arg Arg Ile
1               5                   10                  15

Tyr Asn Asn Arg
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar, hydrophobic, or positive net
      charge residue
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Any positive net charge residue
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Any non-polar, hydrophobic residue
<220> FEATURE:
<221> NAME/KEY: MOD_RES
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (11)..(11)
<223> OTHER INFORMATION: Any positive net charge residue
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
<221> NAME/KEY: MOD_RES
<222> LOCATION: (15)..(15)
<223> OTHER INFORMATION: Any positive net charge residue, Proline,
      or any Proline derivative
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine

```
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
<222> LOCATION: (20)..(20)
<223> OTHER INFORMATION: Any positive net charge residue
<220> FEATURE:
<221> NAME/KEY: MOD_RES
<222> LOCATION: (21)..(21)
<223> OTHER INFORMATION: Proline, any Proline derivative, any positive
      net charge residue, or not present
<220> FEATURE:
<221> NAME/KEY: MOD_RES
<222> LOCATION: (22)..(22)
<223> OTHER INFORMATION: Proline, any Proline derivative, any polar
      residue, any Hydrophobic residue, or not present
<220> FEATURE:
<223> OTHER INFORMATION: See specification as filed for detailed
      description of substitutions and preferred embodiments

<400> SEQUENCE: 6

Xaa Xaa Xaa Xaa Xaa Tyr Xaa Xaa Xaa Xaa Xaa Xaa Xaa Xaa Xaa Thr
1               5                   10                  15

Xaa Xaa Xaa Xaa Xaa Xaa
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arginine, Lysine, delta-hydroxylysine,
      homoarginine, 2,4-diaminobutanoic acid, beta-homoarginine,
      D-Arginine, arginal, 2-amino-3-guanidinopropionate, nitroarginine,
      N-methylarginine, epsilon-N-methyllysine, allo-hydroxylysine,
<220> FEATURE:
<221> NAME/KEY: MOD_RES
<222> LOCATION: (1)..(1)
<223> OTHER INFORMATION: Cont'd; 2,3-diaminopropionate,
      2,2'-diaminopimelic acid, Ornithine, sym-dimethylarginine,
      asym-dimethylarginine, 2,6-Diamino-4-hexynoic acid,
      p-aminobenzoic acid, 3-aminotyrosine, Valine, Isoleucine,
      Leucine, Methionine,
<220> FEATURE:
<221> NAME/KEY: MOD_RES
<222> LOCATION: (1)..(1)
<223> OTHER INFORMATION: Cont'd; Alanine, Phenylalanine,
      N-methyl-leucine, tert.-butylglycine, cyclo-hexylalanine,
      beta-alanine, 1-aminocyclohexylcarboxylate, N-methyl-Isoleucine,
      Norleucine, Norvaline, or N-methylvaline
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Any positive net charge residue
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Any non-polar, hydrophobic residue
<220> FEATURE:
<221> NAME/KEY: MOD_RES
```

```
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (11)..(11)
<223> OTHER INFORMATION: Any positive net charge residue
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
<221> NAME/KEY: MOD_RES
<222> LOCATION: (15)..(15)
<223> OTHER INFORMATION: Any positive net charge residue, Proline,
      or any Proline derivative
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
<222> LOCATION: (20)..(20)
<223> OTHER INFORMATION: Any positive net charge residue
<220> FEATURE:
<221> NAME/KEY: MOD_RES
<222> LOCATION: (21)..(21)
<223> OTHER INFORMATION: Proline, any Proline derivative, any positive
      net charge residue, or not present
<220> FEATURE:
<221> NAME/KEY: MOD_RES
<222> LOCATION: (22)..(22)
<223> OTHER INFORMATION: Proline, any Proline derivative, any polar
      residue, any Hydrophobic residue, or not present
<220> FEATURE:
<223> OTHER INFORMATION: See specification as filed for detailed
      description of substitutions and preferred embodiments

<400> SEQUENCE: 7

Xaa Xaa Xaa Xaa Xaa Tyr Xaa Xaa Xaa Xaa Xaa Xaa Xaa Xaa Xaa Thr
1               5                   10                  15

Xaa Xaa Xaa Xaa Xaa Xaa
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Any non-polar, hydrophobic, or positive net
      charge residue
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Any positive net charge residue
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Any non-polar, hydrophobic residue
<220> FEATURE:
<221> NAME/KEY: MOD_RES
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (11)..(11)
<223> OTHER INFORMATION: Arginine, Lysine, delta-Hydroxylysine,
      Homoarginine, beta-Homoarginine, D-Arginine, arginal,
      2,4-diaminobutanoic acid, 2-amino-3-guanidinopropionic acid,
      nitroarginine, nitrosoarginine, N-methylarginine,
      epsilon-N-methyllysine,
<220> FEATURE:
<221> NAME/KEY: MOD_RES
<222> LOCATION: (11)..(11)
<223> OTHER INFORMATION: Cont'd; allo-hydroxylysine,
      2,3-diaminopropionate, 2,2'-diaminopimelic acid, Ornithine,
      sym-dimethylarginine, asym-dimethylarginine,
      2,6-diamino-4-hexynoic acid, p-aminobenzoic acid, or
      3-aminotyrosine
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
<221> NAME/KEY: MOD_RES
<222> LOCATION: (15)..(15)
<223> OTHER INFORMATION: Any positive net charge residue, Proline,
      or any Proline derivative
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
```

```
<222> LOCATION: (20)..(20)
<223> OTHER INFORMATION: Arginine, Lysine, delta-Hydroxylysine,
      Homoarginine, beta-Homoarginine, D-Arginine, arginal,
      2,4-diaminobutanoic acid, 2-amino-3-guanidinopropionic acid,
      nitroarginine, nitrosoarginine, N-methylarginine,
      epsilon-N-methyllysine,
<220> FEATURE:
<221> NAME/KEY: MOD_RES
<222> LOCATION: (20)..(20)
<223> OTHER INFORMATION: Cont'd; allo-hydroxylysine,
      2,3-diaminopropionate, 2,2'-diaminopimelic acid, Ornithine,
      sym-dimethylarginine, asym-dimethylarginine,
      2,6-diamino-4-hexynoic acid, p-aminobenzoic acid,
      or 3-aminotyrosine
<220> FEATURE:
<221> NAME/KEY: MOD_RES
<222> LOCATION: (21)..(21)
<223> OTHER INFORMATION: Proline, any Proline derivative, any
      positive net charge residue, or not present
<220> FEATURE:
<221> NAME/KEY: MOD_RES
<222> LOCATION: (22)..(22)
<223> OTHER INFORMATION: Proline, any Proline derivative, any
      polar residue, any Hydrophobic residue, or not present
<220> FEATURE:
<223> OTHER INFORMATION: See specification as filed for detailed
      description of substitutions and preferred embodiments

<400> SEQUENCE: 8

Xaa Xaa Xaa Xaa Xaa Tyr Xaa Xaa Xaa Xaa Xaa Xaa Xaa Xaa Xaa Thr
1               5                   10                  15

Xaa Xaa Xaa Xaa Xaa Xaa
            20

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar, hydrophobic, or positive net
      charge residue
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Any positive net charge residue
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Any non-polar, hydrophobic residue
<220> FEATURE:
<221> NAME/KEY: MOD_RES
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
```

```
      Hydroxyproline, or any Hydroxyproline derivative
<220> FEATURE:
<221> NAME/KEY: MOD_RES
<222> LOCATION: (11)..(11)
<223> OTHER INFORMATION: Any positive net charge residue
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
<221> NAME/KEY: MOD_RES
<222> LOCATION: (15)..(15)
<223> OTHER INFORMATION: Arginine, Lysine, delta-hydroxylysine,
      homoarginine, beta-homoarginine, D-Arginine, arginal,
      2,4-diaminobutanoic acid, 2-amino-3-guanidinopropionic acid,
      nitroarginine, nitroso-arginine, N-methylarginine,
      epsilon-N-methyllysine,
<220> FEATURE:
<221> NAME/KEY: MOD_RES
<222> LOCATION: (15)..(15)
<223> OTHER INFORMATION: Cont'd; allo-hydroxylysine,
      2,3-diaminopropionate, 2,2'-diaminopimelic acid, Ornithine,
      sym-dimethylarginine, asym-dimethylarginine,
      2,6-diamino-4-hexynoic acid, p-aminobenzoic acid,
      3-aminotyrosine, Proline, cis-4-hydroxyproline,
<220> FEATURE:
<221> NAME/KEY: MOD_RES
<222> LOCATION: (15)..(15)
<223> OTHER INFORMATION: Cont'd; trans-4-hydroxyproline,
      cis-3-hydroxyproline, trans-3-hydroxyproline,
      beta-cyclohexylalanine, 3,4-cis-methanoproline,
      3,4-dehydroproline, Homoproline, or pseudoproline
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
<222> LOCATION: (20)..(20)
<223> OTHER INFORMATION: Any positive net charge residue
<220> FEATURE:
<221> NAME/KEY: MOD_RES
<222> LOCATION: (21)..(21)
<223> OTHER INFORMATION: Proline, any Proline derivative, any
      positive net charge residue, or not present
<220> FEATURE:
<221> NAME/KEY: MOD_RES
<222> LOCATION: (22)..(22)
<223> OTHER INFORMATION: Proline, any Proline derivative, any polar
      residue, any Hydrophobic residue, or not present
<220> FEATURE:
<223> OTHER INFORMATION: See specification as filed for detailed
      description of substitutions and preferred embodiments

<400> SEQUENCE: 9

Xaa Xaa Xaa Xaa Xaa Tyr Xaa Xaa Xaa Xaa Xaa Xaa Xaa Xaa Xaa Thr
1               5                   10                  15

Xaa Xaa Xaa Xaa Xaa Xaa
            20

<210> SEQ ID NO 10
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar, hydrophobic, or positive net
      charge residue
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Histidine, Lysine, Arginine, Homoarginine,
      or Ornithine
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Any non-polar, hydrophobic residue
<220> FEATURE:
<221> NAME/KEY: MOD_RES
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (11)..(11)
<223> OTHER INFORMATION: Any positive net charge residue
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
<221> NAME/KEY: MOD_RES
<222> LOCATION: (15)..(15)
<223> OTHER INFORMATION: Any positive net charge residue, Proline,
      or any Proline derivative
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
<222> LOCATION: (20)..(20)
<223> OTHER INFORMATION: Any positive net charge residue
<220> FEATURE:
<221> NAME/KEY: MOD_RES
```

```
<222> LOCATION: (21)..(21)
<223> OTHER INFORMATION: Proline, any Proline derivative, any positive
      net charge residue, or not present
<220> FEATURE:
<221> NAME/KEY: MOD_RES
<222> LOCATION: (22)..(22)
<223> OTHER INFORMATION: Proline, any Proline derivative, any polar
      residue, any Hydrophobic residue, or not present
<220> FEATURE:
<223> OTHER INFORMATION: See specification as filed for detailed
      description of substitutions and preferred embodiments

<400> SEQUENCE: 10

Xaa Xaa Xaa Xaa Xaa Tyr Xaa Xaa Xaa Xaa Xaa Xaa Xaa Xaa Thr
1               5                   10                  15

Xaa Xaa Xaa Xaa Xaa Xaa
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar, hydrophobic, or positive net
      charge residue
<220> FEATURE:
<221> NAME/KEY: MOD_RES
<222> LOCATION: (2)..(2)
<223> OTHER INFORMATION: Aspartic acid or Glutamic acid
<220> FEATURE:
<221> NAME/KEY: MOD_RES
<222> LOCATION: (3)..(3)
<223> OTHER INFORMATION: Any positive net charge residue
<220> FEATURE:
<221> NAME/KEY: MOD_RES
<222> LOCATION: (4)..(5)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (7)..(7)
<223> OTHER INFORMATION: Leucine, Isoleucine, Valine or
      tert.-butylglycine
<220> FEATURE:
<221> NAME/KEY: MOD_RES
<222> LOCATION: (8)..(8)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (9)..(9)
<223> OTHER INFORMATION: Any positive net charge residue
<220> FEATURE:
<221> NAME/KEY: MOD_RES
<222> LOCATION: (10)..(10)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (11)..(11)
<223> OTHER INFORMATION: Any positive net charge residue
<220> FEATURE:
<221> NAME/KEY: MOD_RES
<222> LOCATION: (12)..(13)
<223> OTHER INFORMATION: Proline, any Proline derivative,
      Hydroxyproline, or any Hydroxyproline derivative
<220> FEATURE:
<221> NAME/KEY: MOD_RES
<222> LOCATION: (14)..(14)
<223> OTHER INFORMATION: Any positive net charge residue
<220> FEATURE:
```

```
<221> NAME/KEY: MOD_RES
<222> LOCATION: (15)..(15)
<223> OTHER INFORMATION: Any positive net charge residue, Proline,
      or any Proline derivative
<220> FEATURE:
<221> NAME/KEY: MOD_RES
<222> LOCATION: (17)..(17)
<223> OTHER INFORMATION: Tyrosine, Proline, any Proline derivative,
      Hydroxyproline, or any Hydroxyproline derivative
<220> FEATURE:
<221> NAME/KEY: MOD_RES
<222> LOCATION: (18)..(18)
<223> OTHER INFORMATION: Asparagine or Glutamine
<220> FEATURE:
<221> NAME/KEY: MOD_RES
<222> LOCATION: (19)..(19)
<223> OTHER INFORMATION: Asparagine, Glutamine, or absent
<220> FEATURE:
<221> NAME/KEY: MOD_RES
<222> LOCATION: (20)..(20)
<223> OTHER INFORMATION: Any positive net charge residue
<220> FEATURE:
<221> NAME/KEY: MOD_RES
<222> LOCATION: (21)..(21)
<223> OTHER INFORMATION: Proline, any Proline derivative, any
      positive net charge residue, or not present
<220> FEATURE:
<221> NAME/KEY: MOD_RES
<222> LOCATION: (22)..(22)
<223> OTHER INFORMATION: Proline, any Proline derivative, any polar
      residue, any Hydrophobic residue, or not present
<220> FEATURE:
<223> OTHER INFORMATION: See specification as filed for detailed
      description of substitutions and preferred embodiments

<400> SEQUENCE: 11

Xaa Xaa Xaa Xaa Xaa Tyr Xaa Xaa Xaa Xaa Xaa Xaa Xaa Xaa Xaa Thr
1               5                   10                  15

Xaa Xaa Xaa Xaa Xaa Xaa
            20
```

ANTIMICROBIAL PEPTIDES AND PEPTIDE DERIVATIVES DERIVED FROM ONCOPELTUS FASCIATUS

CROSS-REFERENCE TO RELATED APPLICATIONS

The present invention is a National Stage Entry of Serial No. PCT/EP2011/058721, filed May 27, 2011, which claims priority to European Application No. 10164251.0, filed May 28, 2010, the full disclosures of which are hereby incorporated herein by their reference.

TECHNICAL FIELD OF THE INVENTION

The present invention relates to small antimicrobial peptides, particularly to small modified antimicrobial peptides.

SEQUENCE LISTING

The instant application contains a Sequence Listing which has been submitted ASCII format via EFS-Web and is hereby incorporated by reference in its entirety. Said ASCII copy, created on Jan. 8, 2013, is named 0108_0003_US1_Sequence_Listing.txt and is 19,418 bytes in size.

BACKGROUND OF THE INVENTION

The incidence of serious bacterial and fungal infections is increasing despite remarkable advances in antibiotic therapy. Each year there are more than 40 million hospitalizations in the United States, and about 2 million patients acquire nosocomial infections, 50 to 60% of which involve antibiotic-resistant bacteria. The number of deaths related to nosocomial disease is estimated at 60,000-70,000 annually in the USA and up to 10.000 in Germany. Whereas resistant Gram-negative bacteria were a major problem in the 1970s, the 1990s had seen a climb in number of incidents with multi-drug resistant Gram-positive strains. Currently, the rapid emergence of resistant strains involves both Gram-positive and Gram-negative pathogens. Resistances developed first in species in which single mutations were sufficient to cause clinically important levels, such as *Staphylococcus aureus* and *Pseudomonas aeruginosa*, followed by bacteria in which multiple mutations are required, such as *E. coli* and *Neisseria gonorrhoeae*. This is mainly due to the broad use of fluoroquinolones. Important causes of Gram-negative resistance include extended spectrum beta lactamases in *Escherichia coli* and *Klebsiella pneumoniae*. Almost half of the clinical strains of *Haemophilus ducreyi*, the causative agent of chancroid, carries genes to confer resistance to amoxicillin, ampicillin and a series of other β-lactams. Likewise, for *Salmonella enterica* serovar. Typhimurium, resistance towards tetracyclines has increased from zero in 1948 to a 98% level in 1998.

This necessitates a continuing search for novel antibiotics. Inducible antibacterial peptides represent a field of study where contemporary biochemistry, immunology and drug design converge. Peptide antibiotics, ranging in size from 13 to more than a hundred amino acid residues, have been isolated from plants, animals and microbes (Boman, H. G. (1995) Peptide antibiotics and their role in innate immunity. *Annu. Rev. Immunol.* 13: 61-92). The overwhelming majority of antibacterial peptides, including the well-studied defensins, cecropins and magainins, function through a "lytic/ionophoric" mechanism. Common theme among all "lytic" peptides is a permeabilizing effect on bacterial cytoplasmic membranes. Peptides acting directly on the bacterial membrane often have also toxic effects on mammalian membranes at higher concentrations, which limits their potential as future drugs. When prolines are inserted into the sequences of α-helical antimicrobial peptides, the peptides' ability to permeabilize the cytoplasmic membrane of *E. coli* decreases substantially as the function of the number of proline residues incorporated. In this regard, it is intriguing that some of the most active native antibacterial peptides, at least against selected Gram-negative pathogens, belong to the proline-rich peptide family.

Proline-rich antimicrobial peptides, including apidaecin, originally isolated from insects, have been postulated to overcome said shortcuts. Furthermore, modification of specific peptide bonds within the apidaecin has been modified at different positions in order to obtain a peptide being more resistant to cleavage, e.g. by proteases (WO-A 2009/013262). The inventors furthermore found that modification at different positions of an artificial peptide (oncocin; SEQ ID NO. 1)-said peptide is based on the sequence of *Oncopeltus fasciatus* antibacterial peptide 4 (SEQ ID NO. 5)-results in an increased stability against proteases and an additional dramatically enhanced antimicrobial activity (PCT/EP2010/051072; not yet published). However, there is still a need for antimicrobial peptides with an increased stability and enhanced antimicrobial activity.

TABLE 1

| Peptide | Species | Sequence | SEQ ID NO. | Ref. |
|---|---|---|---|---|
| Oncopeltus antibacterial peptide 4 | *Oncopeltus fasciatus* | VDKPPYLPRP(X/P)PPRRIYN(NR) | 5 | [1] |
| Oncocin | artificial | VDKPPYLPRPRPPRRIYNR-NH$_2$ | 1 | [2] |

[1] Schneider M & Dorn A. Differential infectivity of two pseudomonas species and the immune response in the milkweed bug, *Oncopeltus fasciatus* (Insecta: Hemiptera). *Journal of Invertebrate Pathology* 78: 135-40, 2001

[2] (PCT/EP2010/051072; not yet published)

The inventors now unexpectedly found that the substitution of isoleucine at position 16 of oncocin (SEQ ID NO. 1) leads to peptides or peptide derivatives which exhibit a dramatically increased stability and antimicrobial activity when compared with the *Oncopeltus* antibacterial peptide 4 (SEQ ID NO. 5).

BRIEF DESCRIPTION OF THE INVENTION

Thus, the present invention now provides further antimicrobial peptides or peptide derivatives with increased antimicrobial activity and metabolic stability in mammalian serum as well as stability against bacterial proteases. The peptides and peptide derivatives according to the present invention are based on the finding that the substitution of isoleucine at position 16 of *Oncopeltus* antibacterial peptide 4 (SEQ ID NO. 5) or of oncocin (SEQ ID No. 1) by a threonine confers the desired properties to the peptide. Furthermore, additional modifications or substitutions, as will be outlined in great detail herein below, lead to an additional increase in stability and/or antimicrobial activity of the peptides or peptide derivatives. Thus, the problem is solved by the present invention by the provision of a peptide or peptide comprising the following sequence;

(SEQ ID NO: 6)
$Sub_1-X_1-D_2-K_3-P_4-P_5-Y_6-L_7-P_8-R_9-P_{10}-X_2-P_{12}-P_{13}-R_{14}-X_3-T_{16}-N_{18}-N_{19}-X_4-Sub_2$ wherein $Sub_1$ is the N-terminal amino group of $X_1$ or a modified N-terminal amino group of $X_1$; wherein $X_1$ is selected from the group of residues consisting of non-polar, hydrophobic residue and residue with a positive net charge;
wherein $D_2$ is aspartic acid or glutamic acid;
wherein $K_3$, $R_9$ and $R_{14}$ are independently residues with a positive net charge;
wherein at least $P_4$, $P_5$, $P_8$, $P_{10}$, $P_{12}$, and $P_{13}$ are independently chosen from the group consisting of proline, proline derivatives, hydroxyproline and hydroxyproline derivatives;
wherein $Y_6$ is tyrosine;
wherein $L_7$ is a non-polar, hydrophobic residue;
wherein $X_2$ and $X_4$ are independently residues with a positive net charge;
wherein $X_3$ is chosen from the group consisting of residues with a positive net charge, proline, and proline derivatives;
wherein $P_{17}$ is chosen from the group consisting of tyrosine, proline, proline derivatives, hydroxyproline and hydroxyproline derivatives;
wherein $T_{16}$ is threonine;
wherein $N_{18}$ is asparagine or glutamine;
wherein $N_{19}$ is asparagine or glutamine or $N_{19}$ is absent;
wherein $Sub_2$ is selected from the group consisting of the free C-terminal carboxyl group of $X_4$, a modified C-terminal carboxyl group of $X_4$, $X_5$ with a free C-terminal carboxyl group, $X_5$ with a modified C-terminal carboxyl group, $X_5$-$X_6$ with a free C-terminal carboxyl group, and $X_5$-$X_6$ with a modified C-terminal carboxyl group;
wherein $X_5$ is selected from the group consisting of proline, proline derivatives and residues with a positive net charge; and
wherein $X_6$ is selected from the group consisting of proline, proline derivatives, polar residues and hydrophobic residues; with the proviso that if at least 6 of the residues from the group consisting of $D_2$, $P_4$, $P_5$, $P_8$, $P_{10}$, $P_{12}$, $P_{13}$ and $P_{17}$ are as defined above, one or two residues may be exchanged by any other residue. However, in one embodiment of the present invention all residues from the group consisting of $D_2$, $P_4$, $P_5$, $P_8$, $P_{10}$, $P_{12}$, $P_{13}$, and $P_{17}$ are as defined above and are not exchanged by any other residue.

The invention further relates to a multimer comprising at least one peptide or peptide derivative according the present invention.

Furthermore the invention relates to a pharmaceutical composition comprising a peptide or peptide derivative or a multimer according to the present invention. The pharmaceutical composition may further comprise pharmaceutically acceptable adjuvants.

It has been shown that the peptides or peptide derivatives according to the present invention have an antimicrobial activity against microorganisms which are often associated with diseases. Thus, the invention further provides a peptide or peptide derivative or a multimer according to the present invention for use in the treatment of a disease.

Furthermore, due to their antimicrobial activity the peptides and peptide derivatives according to the present invention are well suited for disinfecting and/or cleaning, e.g. surfaces. Furthermore, the peptide or peptide derivatives or multimers according to the present invention are well suited for disinfecting or preserving packages and the respective content of the package, e.g. food stuff. Thus the present invention also relates to the use of a peptide or peptide derivative or a multimer according to the present invention as a disinfectant and/or cleaning agent and/or preservative and/or in packaging material.

BRIEF DESCRIPTION OF THE DRAWINGS

FIG. 1: Cytoxicity assay against HEK 293 (black bars), HepG2 (light grey bars), HeLa (dark grey bars) cells determined with the Cell Proliferation Kit I (Roche) for peptide concentrations of 600 µg/mL and incubation times of 24 hrs. The positive controls contained DMSO (12%) or melittin (100 µg/mL). Values were normalized to 12% PBS as negative control. Reference examples are marked with an asterisk.

DETAILED DESCRIPTION OF THE INVENTION

In context of the present invention a "residue" is a moiety that can form a covalent bond with both the COOH-group of the preceding amino acid residue and the $NH_2$-group of the following (amino acid) residue. Thus, a peptide backbone may be formed. However, the covalent bondings of the residue to said COOH-group and $NH_2$-group do not necessarily need to maintain a continuous peptide backbone structure, e.g. they may result in an altered backbone structure sugar amino acid dipeptide isosters, azapeptides, δ-homopolymers, γ-peptides, γ-lactam analogues, oligo(phenylene ethylene)s, vinylogous sulfonopeptides, poly-N-substituted glycines, or oligocarbamates or a backbone with one or more non cleavable bonds like amide bond, an alkylated amide bond, or a thioamide bond. However, in a preferred embodiment of the present invention the term "residue" includes all amino acids, i.e. natural amino acids (or proteinogenic amino acids), non natural amino acids and amino acid derivatives (like imino acids) are meant. A residue, e.g. an amino acid, may be present in L- or D-configuration (for isoleucine and threonine in the D-allo configuration (only inversion at one of the chiral centers)). However, if not otherwise specified, the amino acids in the sequences are in the L-configuration.

The term "peptide" as used herein means a sequence of amino acids or amino acid derivatives as disclosed herein linked by a peptide bond.

The term "peptide derivative" (or peptidomimetics) in context of the present invention includes peptides, which are modified, e.g. on the N- or C-terminus by the groups Sub and $Sub_2$ as defined herein, and comprises peptides altered by substitutions and/or modifications of one or more of the amino acid residues by moieties other than natural protein-building amino acid residues, such as non-proteinogenic α-amino acids, β-amino acids, or peptides with an altered backbone. Altered back bone in a preferred embodiment means at least one peptide bond has been replaced by e.g. a non-cleavable bond like a reduced amide bond, an alkylated amide bond, or a thioamide bond. A non-cleavable bond is defined as a bond, which is not susceptible to cleavage by proteases and is preferably selected from the group consisting of a reduced amide bond, alkylated amide bond, or a thioamide bond. A reduced amide bond is a peptide bond, in which the carbonyl moiety (C=O) is either reduced to a hydroxyl moiety (HCOH) or a methylene moiety ($CH_2$). An alkylated amide bond is a peptide bond in which either the nitrogen (N-alpha) or the carbon (C-alpha) is substituted with alkyl, preferably with 1 to 3 C-atoms, a preferred example being N-methylation.

A residue having a positive net charge is defined as a residue, e.g. an amino acid or amino acid derivative, having a positively charged side chain under physiological conditions. Physiological conditions are defined as pH 7.35 to 7.45, preferably pH 7.4, 37° C. and an osmotic pressure of 280 to 300 mosmol/kg, preferably about 300 mosmol/kg. A positively charged side chain is defined as a side chain bearing at least one positive polar group (e.g amino, amide or guanidino group) that allows the formation of a hydrogen bond with a negative polar group (e.g. a hydroxyl group). A moiety having a net positive charge is preferably a basic amino acid residue. Preferred residues having a positive net charge are selected from the group of residues consisting of arginine, histidine, lysine, δ-hydroxylysine, homoarginine, 2,4-diaminobutanoic acid, β-homoarginine, D-arginine, arginal, 2-amino-3-guanidinopropionate, nitroarginine, N-methylarginine, ε-N-methyllysine, allo-hydroxylysine, 2,3-diaminopropionate, 2,2'-diaminopimelic acid, ornithine, sym-dimethylarginine, asym-dimethylarginine, 2,6-diamino-4-hexynoic acid, p-aminobenzoic acid, and 3-aminotyrosine.

A non-polar, hydrophobic residue according to the present invention is a residue, e.g. an amino acid or amino acid derivative, having a non-charged, hydrophobic side chain under physiological conditions. Physiological conditions are defined as pH 7.35 to 7.45, preferably as pH 7.4, 37° C. and an osmotic pressure of 280 to 300 mosmol/kg, preferably about 300 mosmol/kg. A non-polar, hydrophobic residue is preferably a neutral residue without polar groups in the aliphatic or aromatic amino acid side chain, preferably being more hydrophobic than alanine. Preferred non-polar residues are selected from the group of residues consisting of leucine, methionine, phenylalanine, tryptophan, tyrosine, isoleucine, valine, N-methyl-leucine, tert.-butylglycine, cyclo-hexylalanin, β-alanine, 1-aminocylcohexylcarboxylate, N-methyl-isoleucine, norleucine, norvaline and N-methylvaline.

A proline derivative is a structure containing a substituted or unsubstituted pyrrolidine-ring derived from proline. Preferred proline derivatives are selected from the group of residues consisting of 3,4-cis-methanoproline, 3,4-dehydroproline, homoproline, and pseudoproline. In one embodiment of the invention $N_{19}$ of Formula 1 is absent and thus the peptide or peptide derivative comprises the following sequence:

$Sub_1$-$X_1$-$D_2$-$K_3$-$P_4$-$P_5$-$Y_6$-$L_7$-$P_8$-$R_9$-$P_{10}$-$X_2$-$P_{12}$-$P_{13}$- $P_{14}$-$X_3$-$T_{16}$-$P_{17}$-$N_{18}$-$X_4$-$Sub_2$ (formula 2)

In one embodiment of the present invention $Sub_1$ is a free N-terminal amino group of the amino acid $X_1$ or a modified N-terminal amino group (replacing the N-terminal amino group of the amino acid $X_1$ sequence by $Sub_1$) with the general formula $NR_1R_2$. $Sub_1$=$NR_1R_2$, whereas $R_1$ and $R_2$ are independently selected from hydrogen or the groups consisting of a unbranched alkyl, branched alkyl, cyclic or heterocyclic alkyl group, such as methyl, ethyl, n-propyl, isopropyl, n-butyl, isobutyl, or cyclohexyl; an unbranched alkonyl, branched alkonyl, cyclic or heterocyclic alkanoyl group, such as acetyl or methanoyl (formyl), propionyl, n-butyryl, isobutyryl, pentanoyl, hexanoyl, or cyclohexanoyl; and a reporter group, such as a fluorescent dye (e.g. fluorescein, Alexa488) or biotin.

In one embodiment $Sub_1$ is a modified N-terminal amino group of $X_1$ selected from the group consisting of acyl-NH— and acetyl-NH—.

In a preferred embodiment $Sub_1$ is the free N-terminal amino group of $X_1$.

In one embodiment $R_1$ is a hydrogen and $R_2$ is the carbon atom of $COR_3$ ($Sub_2$; see underneath) bridging the N- and C-terminus of the peptide to obtain a cyclic peptide.

In a further embodiment $Sub_1$ is a modified N-terminal amino group of $X_1$ selected from the group consisting of acyl-NH—, acetyl-NH—, guanidino-, alkyl-, and oligodialkylguanidino, methyl ester, ethyl ester, propyl ester, butyl ester, cyclohexyl ester, methyl amine, ethyl amine, propyl amine, butyl amine and cyclohexyl amine.

In one embodiment of the present invention $X_1$ is selected from the group of residues consisting of arginine, lysine, δ-hydroxylysine, homoarginine, 2,4-diaminobutanoic acid, p-homoarginine, D-arginine, arginal, 2-amino-3-guanidinopropionate, nitroarginine, N-methylarginine, ε-N-methyllysine, allo-hydroxylysine, 2,3-diaminopropionate, 2,2'-diaminopimelic acid, ornithine, sym-dimethylarginine, asym-dimethylarginine, 2,6-diamino-4-hexynoic acid, p-aminobenzoic acid, 3-aminotyrosine, valine, isoleucine, leucine and methionine, alanine, phenylalanine, N-methylleucine, tert.-butylglycine, cyclo-hexylalanin, β-alanine, 1-aminocylcohexylcarboxylate, N-methyl-isoleucine, norleucine, norvaline and N-methylvaline.

In a preferred embodiment $R_9$ and $R_{14}$ are independently selected from the group consisting of arginine, homoarginine, lysine, and ornithine In a further embodiment of the invention $X_2$ and $X_4$ are independently selected from the group of residues consisting of arginine, lysine, δ-hydroxylysine, homoarginine, β-homoarginine, D-arginine, arginal, 2,4-diaminobutanoic acid, 2-amino-3-guanidinopropionic acid, nitroarginine, nitrosoarginine, N-methylarginine, ε-N-methyllysine, allo-hydroxylysine, 2,3-diaminopropionate, 2,2'-diaminopimelic acid, ornithine, sym-dimethylarginine, asym-dimethylarginine, 2,6-diamino-4-hexynoic acid, p-aminobenzoic acid, and 3-aminotyrosine.

$X_3$, in one embodiment of the invention, is selected from the group of residues consisting of arginine, lysine, δ-hydroxylysine, homoarginine, β-homoarginine, D-arginine, arginal, 2,4-diaminobutanoic acid, β-homoarginine, 2-amino-3-guanidinopropionic acid, nitroarginine, nitrosoarginine, N-methylarginine, ε-N-methyllysine, allo-Hydroxylysine, 2,3-diaminopropionate, 2,2'-diaminopimelic acid, ornithine, sym-dimethylarginine, asym-dimethylarginine, 2,6-diamino-4-hexynoic acid, p-aminobenzoic acid, 3-amino tyrosine, proline, cis-4-hydroxyproline, trans-4-hydroxyproline (4tHyp), cis-3-hydroxyproline, trans-3-hydroxyproline, β-cyclohexylalanine, 3,4-cis-methanoproline, 3,4-dehydroproline, homoproline, and pseudoproline.

In a preferred embodiment of the present invention $X_3$ is selected from the group of residues consisting of ornithine and trans-4-hydroxyproline (4tHyp).

In a preferred embodiment of the present invention $K_3$ is selected from the group of residues consisting of histidine, lysine, arginine, homoarginine, and ornithine.

In one embodiment $L_7$ is selected from the group of residues consisting of leucine, isoleucin, valine, and tert.-butylglycine.

$Sub_2$ is selected from the group consisting of the free C-terminal carboxyl group of $X_4$, a modified C-terminal carboxyl group of $X_4$, $X_5$ with a free C-terminal carboxyl group, $X_5$ with a modified C-terminal carboxyl group, $X_5$-$X_6$ with a free C-terminal carboxyl group, and $X_5$-$X_6$ with a modified C-terminal carboxyl group;

wherein $X_5$ is selected from the group consisting of proline, proline derivatives and residues with a positive net charge; and wherein $X_6$ is selected from the group consisting of proline, proline derivatives, polar residues and hydrophobic residues.

In a preferred embodiment $P_{17}$ is tyrosine.

A modified C-terminal carboxyl group in the context of the present application has the general formula $COR_3$ ($R_3$ replacing the hydroxyl group of the last amino acid) $X_4$—$COR_3$ or $X_5$—$COR_3$ or $X_5X_6$—$COR_3$. wherein $R_3$ is selected from the group consisting of alkoxy, an amine, $NH_2$, an imide, lysine, hydroxylysine, ornithine, 2,4-diaminobutanoic acid, 2,3-diaminopropionic acid, 2,2'-diaminopimelic acid, desmosin, isodesmosine.

In a preferred embodiment $Sub_2$ is selected from the group consisting of a modified C-terminus of $X_4$, $X_5$ with a modified C-terminal carboxyl group, $X_5$-$X_6$ with a modified C-terminal carboxyl group, wherein the modified C-terminus is —$NH_2$.

In a further preferred embodiment $Sub_2$ is a modified C-terminus of $X_4$, wherein the modified C-terminus is —$NH_2$. In a yet further preferred embodiment $Sub_1$ is the free N-terminal amino group of $X_1$ and $Sub_2$ is a modified C-terminus of $X_4$, wherein the modified C-terminus is —$NH_2$. In a yet further preferred embodiment $Sub_1$ is the free N-terminal amino group of $X_1$ and $P_{17}$ is tyrosine and $Sub_2$ is a modified C-terminus of $X_4$, wherein the modified C-terminus is —$NH_2$.

In one embodiment of the present invention $R_3$ is the amino group of $Sub_1$ bridging the N- and C-terminus of the peptide or peptide derivative to obtain a cyclic peptide.

C-terminal peptide derivatives can be in particular formed as an ester ($R_3$=alkoxy), an amide ($R_3$=amine), an imide (also called secondary amine, or imine), or a peptide elongated by additional amino acids selected from the group consisting of Pro, Ile, Arg, Val modified again at the C-terminal end as ester, amide, or imide. Further peptide derivatives can be formed by modifications at the N-terminal or C-terminal ends of the peptide. These changes can, for instance, be addition of an alkyl or alkanoyl group (either having a straight chain or being branched or cyclic or heterocyclic) or a guanidino group or addition of a macromolecule or a reporter moiety, either via a permanent linkage or a connection that can be cleaved under certain conditions (such as disulfide bridges or acid labile linkers).

In one preferred embodiment the peptide or peptide derivative is selected from the group consisting of SEQ ID NO. 2 and SEQ ID NO. 3.

It is one embodiment of the present invention that the peptide or peptide derivative exhibits an increased stability against peptidase and protease degradation. The skilled artisan knows modification of the peptide or peptide derivative resulting in such increased stability, e.g. the peptide backbone may comprise one or more modified peptide bonds. Thus, in a preferred embodiment at least one peptide bond of the peptide backbone of the peptide or peptide derivative according to the present invention is a modified peptide bond. Modifications of peptide bonds suited are well known by those skilled in the art. In one embodiment of the present invention at least one modified peptide bond is selected from the group consisting of a reduced amide bond, alkylated amide bond, and thio-amide bond. In a preferred embodiment one or more of the peptide bonds between $R_{14}$ and $R_{15}$, between $N_{18}$ and $R_{19}$, between $V_1$ and $D_2$, and between $D_2$ and $K_3$ are modified peptide bonds. In a further preferred embodiment two or more of the peptide bonds between $R_{14}$ and $R_{15}$, between $N_{18}$ and $R_{19}$, between $V_1$ and $D_2$, and between $D_2$ and $K_3$ are modified peptide bonds. In yet a further preferred embodiment three or more of the peptide bonds between $R_{14}$ and $R_{15}$, between $N_{18}$ and $R_{19}$, between $V_1$ and $D_2$, and between $D_2$ and $K_3$ are modified peptide bonds. In another preferred embodiment all peptide bonds between $R_{14}$ and $R_{15}$, between $N_{18}$ and $R_{19}$, between $V_1$ and $D_2$, and between $D_2$ and $K_3$ are modified peptide bonds.

As outlined above, the free N-terminal amino group and C-terminal carboxyl group are preferably modified, as these termini are prone to peptidase and protease degradation in serum, body fluids in general, tissues, organs, or cells, and appear to be very critical for the antibiotic activity of the peptides, peptide derivatives and multimers thereof. Increasing the protease resistance increases the half-life of the peptide in the serum. Additionally, modification of the termini also allows for coupling of the peptide to other moieties, such as other amino acid sequences (thereby possibly creating multimeric peptides or proteins), or other biomolecules which can function as carrier or label. In one embodiment of the present invention the peptide or peptide derivative according to the invention is linked to a further peptide at its N-terminus. In a further preferred embodiment the peptide or peptide derivative is fused to a further peptide, said further peptide allowing the penetration of the bacterial cell through the cell membrane. Thus, in on embodiment the peptide or peptide derivative according to the present invention is fused to a further peptide, wherein the further peptide is a cell-penetrating peptide. Cell penetrating peptides are well known by those skilled in the art (Handbook of Cell-Penetrating Peptides, sec. edition (Ed. Ülo Langel, CRC Taylor & Friends, ISBN 0-8493-5090-5)). It is especially preferred that the cell-penetrating peptide allows the penetration of a bacterial cell but not the penetration of a eukaryotic, e.g. a mammalian cell. Such peptides are known by those skilled in the art and, e.g., may be selected from the group consisting of penetratin, Tat-peptides, model amphipathic peptides, transportan, SynB and cis-γ-ammino-L-proline-derived peptides.

In a preferred embodiment the peptide or peptide derivative according to the present invention is bound to a carrier. Suitable carriers may enhance stability or delivery, improve the production, or change the activity spectrum of the peptide. Examples for carriers are human albumin, polyethylene glycol, other biopolymers or other naturally or non-naturally occurring polymers. In one embodiment, the carrier is a further peptide or a protein. In a further embodiment the carrier is able to increase the stability of the peptide or peptide derivative. One of skill in the art can readily select an appropriate carrier. In a preferred embodiment the carrier is a carrier peptide or carrier protein.

In a specific embodiment the carrier molecule also functions as a targeting molecule. Targeting molecules localize the bacterial infection and/or bind to the bacterium, in order to bring the peptide or peptide derivative according to the invention in the vicinity of the bacterial cell to attack or even transport it through the bacterial membrane into the bacterial cell. Such targeting molecules can be molecules binding to lipopolysaccharides (LPS), which form the outside of Gram-negative bacteria. Known compounds for this use are, for instance, anchor peptides, such as the AcmA motif of *Lacto-*

*bacillus*, or antibodies or fragments thereof directed to lipopolysaccharide. In a preferred embodiment the targeting molecule is a antibody or fragment thereof specifically binding to LPS.

The skilled artisan will unambiguously recognize that the further peptide linked to the peptide according to the present invention may be linked directly to the free N-terminus or modified N-terminus or a side chain of a residue, or the further peptide may be linked through a linker. In a preferred embodiment of the present invention the peptide or peptide derivative and the further peptide are linked through a linker. The linker e.g. may be selected from the group of linkers consisting of one or more peptides and polyethyleneglycol (PEG). Preferred linkers in context of the present invention are amino acids or amino acid sequences or chemical compounds that do not sterically hinder the peptides to which they are bound or which they link, i.e. preferred linkers are flexible linkers, e.g. glycine and/or serine rich sequence stretches. Preferred linker sequences are repeats of Gly-Ser.

The present invention includes a multimer comprising at least two peptides or peptide derivatives according to the present invention. The peptides and peptide derivatives according to the invention can be used alone, or in combination, or in form of a linear multimer or in form of a branched multimer. The peptides or peptide derivatives according to the invention may be linked to each other in series forming a unitary peptide, optionally two or more of the peptides or peptide derivatives may be linked via linkers (or spacers), for instance in the form of a peptide dimer, a peptide trimer, etc. Branched multimers may be formed by linking of multiple peptides or peptide derivatives according to the present invention to a carrier individually, i.e. each peptide or peptide derivative is directly linked to a carrier protein, optionally via a linker. The multimer according to the present invention can be composed by peptides and peptide derivatives according to the present invention with identical sequences or of different sequences according to Formula 1 or Formula 2. In a further embodiment the multimer comprises at least two peptides, at least one or more of the peptides are attached to a carrier. In another embodiment, one or more of said peptides is fused to a carrier protein. Still alternatively multiple of the above-described peptides with or without flanking sequences, may be combined sequentially in a polypeptide.

In yet another embodiment, the multimer according to the present invention is in form of a so called multiple antigenic peptide ("MAP"), which can e.g. be designed according to the "MAP-system" as described by Tam et al. (Tam, J. P. (1998) Synthetic Peptide Vaccine Design: Synthesis and Properties of a High-Density Multiple Antigenic Peptide System, *Proc. Natl. Acad. Sci. USA* 85: 5409-5413). This system makes use of a core matrix of lysine residues onto which multiple copies of the same peptide of the invention are synthesized as described (see, e.g. Posnett, D. N., McGrath, H. and Tam, J. P. (1988) A novel method for producing anti-peptide antibodies. Production of site-specific antibodies to the T cell antigen receptor beta-chain. *J. Biol. Chem.* 263: 1719-1725). Each MAP contains multiple copies of one or more of the peptides of this invention. One embodiment of a MAP contains at least three, and preferably four or more peptides. One of skill in the art may readily make any number of multimers from the peptides of the formula identified above with resort to only conventional skills and knowledge in light of this specification. All such multimers are intended to be included in this invention.

Yet other forms of multimers are formed by beads on the surface of which the peptides or peptide derivatives of the invention are exposed. The bead may then function as a carrier for the peptides or peptide derivatives, and may similarly function as a detectable label. Multimers can, for example, be prepared by biotinylating the N-terminus of peptides or peptide derivatives and subsequent complexation with streptavidin. As streptavidin is able to bind four biotin molecules or conjugates with high affinity, very stable tetrameric peptide complexes can be formed by this method. Multimers may be composed of identical or different peptides or peptide derivatives according to the invention. Preferably, however, the multimers of the invention are composed of two or more peptides or peptide derivatives, in which each component constitutes to one asset of the total biocidal activity (targeting, antimicrobial activity, scavenging).

As one embodiment, multiple peptides of the multimer are linked sequentially, optionally through one or more linkers (see above), to form a recombinant polypeptide. Alternatively, the recombinant polypeptide in a further embodiment is linked to a carrier protein, optionally through one or more linkers.

In another embodiment the multimer contains at least two peptides or peptide derivatives according to the present invention, wherein the peptides or peptide derivatives are linked via at least one residue of each of the peptide or peptide derivative, wherein said peptides or peptide derivatives are linked by a covalent bound between the side chains and/or the peptide backbone of said residues.

The present invention also relates to a pharmaceutical composition comprising a peptide or peptide derivative or a multimer according to the present invention. In the practice of one aspect of the present invention, a pharmaceutical composition as described may be administered to a mammal by any route which provides a sufficient level of a peptide and/or peptide derivative and/or multimer according to the present invention. It can be administered systemically or locally. Such administration may be parenterally, transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated. In cases of treating the nervous system this administration route includes, but is not limited to, the intracerebral, intraventricular, intracerebroventricular, intrathecal, intracisternal, intraspinal and/or peri-spinal routes of administration, which can employ intracranial and intravertebral needles, and catheters with or without pump devices.

In one embodiment the pharmaceutical compositions comprise a therapeutically effective amount of a peptide and/or peptide derivative and/or multimer according to the present invention and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "pharmaceutical carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include but are not limited to starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the peptide and/or peptide derivative and/or multimer according to the present invention, preferably in purified form, together with a suitable amount of carrier so as to provide the form for proper administration to the patient. The formulation should suit the mode of administration.

In one embodiment a compound of the invention is administered in a transmucosal dosage form. This route of administration is non-invasive and patient-friendly; at the same time it probably leads to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This is achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

The peptides or peptide derivatives or multimers according to the present invention may also be comprised in a pharmaceutical composition as a pharmaceutically acceptable salt. Pharmaceutically acceptable salts of peptides or peptide derivatives or multimers according to the present invention are prepared by known methods, which typically involve the mixing of the peptide or peptide derivative or multimer with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for ex vivo applications can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. A thorough discussion of pharmaceutically acceptable recipients is available in Remington's Pharmaceutical Sciences (Mack Pub. Co., N.J., 1991). Moreover, also pharmaceutically acceptable solvates are encompassed.

The term "therapeutically effective amount" as used herein refers to an amount of a therapeutic that is a peptide or peptide derivative or multimer according to the present invention, to reduce or prevent growth and colonization of bacteria, or to exhibit a detectable therapeutic or prophylactic effect. The effect can be detected by, for example, culturing biopsies and assaying for bacterial activity or by any other suitable method of assessing the progress or severity of a bacterial infection. The precise effective amount for a subject will depend upon the subject's size and health, the nature and extent of the condition, and the therapeutics or combination of therapeutics selected for administration. Specifically, the compositions of the present invention can be used to reduce or prevent bacterial infection and/or accompanying biological or physical manifestations, such as reduction of fever. Methods that permit the clinician to establish initial dosages are known in the art. The dosages determined to be administered must be safe and efficacious.

Selection of the preferred effective dose will be determined by a skilled artisan based upon considering several factors which will be known to one of ordinary skill in the art. Such factors include the particular form of the pharmaceutic composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient according to standard clinical techniques.

It has been shown that the peptide and peptide derivative and multimer according to the present invention are well suited for medical use. Thus, the present invention also relates to a peptide and/or peptide derivative and/or multimer according to the present invention for use in the treatment of a disease. In a preferred embodiment the disease is selected from the group consisting of bacterial infections, fungal infections. In a further preferred embodiment of the present invention the bacterial infection is an infection with a bacterium selected from the group consisting of *Escherichia coli, Enterobacter cloacae, Erwinia amylovora, Klebsiella pneumoniae, Morganella morganii, Salmonella typhimurium, Salmonella typhi, Shigella dysenteriae, Yersinia enterocolitica, Acinetobacter calcoaceticus, Acinetobacter baumannii, Agrobacterium tumefaciens, Francisella tularensis, Legionella pneumophila, Pseudomonas syringae, Rhizobium meliloti, Pseudomonas aeruginosa, Proteus vulgaris, Proteus mirabilis, Stenotrophomonas maltophilia, Haemophilus influenzae,* and *Micrococcus luteus.*

Next to therapeutic use for treatment of diseases, also in biological warfare, it is also possible to use the peptides and/or peptide derivatives and/or multimers of the invention in a disinfecting or cleaning agent (e.g., a bactericidal composition), which can be used to disinfect or clean surfaces and/or equipment. Another field of application is in packaging, where peptides can be linked to or embedded in packaging material or as a preserving agent for other material which is easily degradable by micro-organisms. The peptides or peptide derivatives of the invention are specifically usable for packaging of food, since they are not toxic upon contact or ingestion. Thus the present invention also relates to the use of a peptide and/or peptide derivative and/or multimer according to the present invention as a disinfectant and/or cleaning agent and/or preservative and/or in packaging material.

Another part of the invention provides a method of treating a mammalian microbial (in particular bacterial or fungal) infection comprising administering to a mammal having said infection an effective an antimicrobial amount of a pharmaceutical composition described herein. In one embodiment the mammal is a non-human mammal.

Methods for producing a peptide or peptide derivatives are known by those skilled in the art. The peptides or peptide derivatives of the invention can be produced synthetically or, where applicable, recombinantly by conventional methods. Preferably, the peptides or peptide derivatives of the invention are prepared conventionally by known chemical synthesis techniques, such as, for instance, are disclosed by Merrifield (Merrifield, R. B. (1963) Solid Phase Peptide Synthesis. I. The Synthesis of a Tetrapeptide J. Am. Chem. Soc. 85: 2149-2154). Due to the small size of the peptides of the present invention, the entire peptide synthesis technologies can be utilized to chemically synthesize such substances. The chemical synthesis can be carried out on a solid support using solid-phase technologies, or, alternatively, in solution phase, both being standard methods known to the skilled person. Peptides according to the invention can also be synthesized by the ligation of two or more side chain-protected or side chain-unprotected fragments, both being standard methods known to the skilled person (Tam J. P., Biopolymers, 2001, 60, 194-205). The solid-phase synthesis of peptides according to the invention or its fragments can be carried out using the Fmoc/tBu- or Boc/Bzl-protection pattern of amino acids. Other protective groups that are not in the standard Fmoc-protection scheme can be used. Purification of synthetic peptides is achieved by chromatographic methods such as reverse-phase, ion exchange or size-exclusion. The chemical methods for the chemical synthesis of the peptides of the invention mentioned here are surveyed in several review publications (examples: Chan W. C. et al. (editors), Fmoc solid phase peptide synthesis: A practical approach, Oxford University Press, Oxford, 2000; Seewald N. et al., Peptides: biology and chemistry, Wiley-VCH, Weinheim, 2002; Goodman, M., Felix, A., Moroder, L., Toniolo, C. (editors) Houben-Weyl, Methods of Organic Chemistry, Synthesis of peptides and peptidomimetics, Georg Thieme Verlag, Stuttgart 2002).

Alternatively, the peptides of the invention may be produced by recombinant DNA techniques by cloning and expressing within a host microorganism or cell a DNA fragment carrying a nucleic acid sequence encoding one of the above-described peptides. Nucleic acid coding sequences can be prepared synthetically (Stemmer, W. P., Crameri, A., Ha, K. D., Brennan, T. M., Heyneker, H. L. (1995) Single-step assembly of a gene and entire plasmid from large numbers of oligodeoxyribonucleotides. Gene 164: 49-53), or may be derived from existing nucleic acid sequences (e.g. the sequence coding for wild-type apidaecin) by site-directed mutagenesis. The so prepared coding sequences can be amplified from RNA (or DNA) using accordingly designed primers in a polymerase chain reaction (PCR) by known techniques. After purification by agarose gel electrophoresis for example, the PCR product is ligated in a vector, and in a host cell finally transformed with the appropriate recombinant plasmid. Various host cells are well known in recombinant technology, such as *E. coli, Bacillus, Lactobacillus, Streptomyces,* mammalian cells (e.g. Chinese Hamster ovary cells (CHO) or COS-1 cells), yeasts (e.g. *Saccharomyces, Schizophyllum*), insect cells or viral expression systems (e.g. baculovirus systems). The selection of other suitable host cells and methods for transformation, culture, amplification, screening, product production and purification can be performed by one of ordinary skills in the art by reference to known techniques (Gething, M. J. and Sambrook, J. (1981) Cell-surface expression of influenza haemagglutinin from a cloned DNA copy of the RNA gene. Nature. 293: 620-625). When produced by conventional recombinant means, the peptides of this invention may be isolated either from the host cell by conventional lysis techniques or from cell medium by conventional methods, such as liquid chromatography, preferably affinity chromatography. The antimicrobial peptide can be expressed as a single peptide, or as an oligomer of several peptide sequences combined either N- or C-terminally, or even an N- or C-terminal tag to allow easier purification of the recombinant peptide or protein constructs. Conventional molecular biology techniques and site-directed mutagenesis may be further employed to modify the sequences and provide desired non-native peptide sequences. All these recombinant techniques are known to the skilled person and have been reported for many antimicrobial peptides, e.g. apidaecin (Maeno, M., Taguchi, S., Momose, H. (1993) Production of antibacterial peptide 'apidaecin' using the secretory expression system of Streptomyces. Biosci. Biotechnol. Biochem. 57: 1206-1207), perinerin (Zhou, Q. F., Luo, X. G., Ye, L., Xi, T. (2007) High-level production of a novel antimicrobial peptide perinerin in *Escherichia coli* by fusion expression. Curr. Microbiol. 54: 366-370), and defensin (Si, L. G., Liu, X. C., Lu, Y. Y., Wang, G. Y., Li, W. M. (2007) Soluble expression of active human beta-defensin-3 in *Escherichia coli* and its effects on the growth of host cells. Chin. Med. J. (Engl). 120: 708-713).

It is also possible to include non-naturally occurring amino acids in peptides through genetic engineering techniques. This has been extensively described by Noren et al. and Ellman et al. (Noren, C. J., Anthony-Cahill, S. J., Griffith, M. C. and Schultz, P. G. (1989) A general method for site-specific incorporation of unnatural amino acids into proteins. Science 244: 182-188; Ellman, J., Mendel, D., Anthony-Cahill, S., Noren, C. J., Schultz, P. G. (1991) Biosynthetic method for introducing unnatural amino acids site-specifically into proteins. Meth. Enzymol. 202: 301-336)

Subsequently, the peptide can be isolated from the culture of the host cells or the in-vitro translation system. This can be achieved by common protein purification and isolation techniques which are state of the art. Such techniques may for example involve immuno-adsorption or -chromatography. It is also possible to provide the peptides with a tag (such as a histidine tag) during synthesis, which allows for a rapid binding and purification, after which the tag is enzymatically removed to obtain the active peptide.

If the peptide itself cannot be encoded or expressed but is very similar to a peptide that can be encoded or expressed, the method can be applied to prepare the peptide to which the peptide is similar, followed by one or more steps in which said peptide is modified by chemical or enzymatic techniques to prepare the final peptide or peptide derivative. Some more comprehensive summaries of methods which can be applied in the preparation of the peptides are described in the literature (W. F. Anderson (1998) Human gene therapy. *Nature* 392 Supp., 25-30; Pharmaceutical Biotechnology (Ed. D. J. A. Crommelin and R. D. Sindelar), Harwood Academic Publishers, 1997, pp. 8-20, 53-70, 123-152, 167-180; Protein Synthesis: Methods and Protocols, Ed. R. Martin, Humana Press, 1998, pp. 1-442; Amino Acid and Peptide Synthesis, Oxford University Press, 1997, pp. 1-89; Solid-Phase Peptide Synthesis (Ed. G. B. Fields) Academic Press, 1997, p. 1-780)

Another object of the invention is the use of a peptide or peptide derivative or a multimer according to the invention in biotechnical or pharmaceutical research or in a screening assay, in particular for identifying a compound, which has a potential bactericidal or antifungal effect.

In a preferred embodiment of the present invention the competitive method of testing at least one compound for anti-microbial properties comprises the following steps:
  (i) contacting
    (a) a microorganism with
    (b) a peptide or peptide derivative according to any one of claims 1 to 17 or a multimer according to claim 18, wherein the peptide or peptide derivative or a multimer reduces the growth rate of said microorganism,
    (c) under condition that allow the formation of a complex between said peptide or peptide derivative or a multimer and its target;
  (ii) subjecting at least one test compound to the complex derived in step (i); and
  (iii) monitoring changes in complex formation and/or complex stability; and
  (iv) determining a compound as capable of modulating complex formation and/or stability based on its ability to change complex formation between the peptide or peptide derivative and the target;
  (v) attributing changes in complex formation and/or complex stability to anti-microbial properties of the at least one test compound.

This screening method identifies test compounds which compete with the peptides, peptide derivatives or multimers of this invention for binding to the unknown receptor or target on or in the pathogen. Thus small molecules specifically binding to the same site targeted by the peptide can be effectively identified in a high-throughput screening. Thereby, the test compounds posses most likely same mode of action as the original peptide sequence and thus will be active also against multiresistant microbes killed by oncocin or one of its analogs described in this invention.

This screening method is carried out by known means, however using at least one peptide or peptide derivative or multimer according to the invention. In one embodiment the peptide or peptide derivative or multimer is labeled with a fluorescent, radioactive or other marker and the binding of the labeled peptide or peptide derivative or multimer to the microorganism is detected and compared in presence or absence of the substance(s) to be tested.

Preferably thereafter, the test compounds, which compete with the peptides or multimeric constructs of this invention for binding to the receptor are identified and screened for anti-bacterial or antifungal use.

In one embodiment the bimolecular fluorescence complementation (BIFC) method is used in the competitive assay. This method enables the direct visualization of intracellular protein interactions, which was exemplified for the interaction of the SH3 domain from the c-Abl tyrosine kinase with both natural and designed targets in *E. coli* (Morell, M., Espargaró, A., Avilés, F. X. and Ventura, S. (2007) Detection of transient protein-protein interactions by bimolecular fluorescence complementation: The Abl-SH3 case. Proteomics 7: 1023-1036). The assay is sensitive enough to enable the detection of interactions between proteins and/or peptides that are poorly expressed in bacteria. It bases on the association of two fragments of the functional yellow fluorescent protein (YFP) after the SH3 domain bound to its partner. Once these two proteins bind to each other, the two fragments of YFP form a complex very similar to the structure of the native protein. This can be monitored by the obtained fluorescence of the YFP complex, as the individual fragments do not show any fluorescence activity. A similar construct can be designed to screen for compounds competing with the peptides and peptide derivatives described in this invention (Morell, M., Czihal, P., Hoffmann, R., Otvos, L., Avilés, F. X. & Ventura, S (2008) Monitoring the interference of protein-protein interactions in vivo by bimolecular fluorescence complementation (BIFC): the DnaK case. Proteomics, 8(17): 3433-42). A high-throughput screening can be easily adapted to 96-well or 386-well microtiter plates or even plates with a higher number of wells by one of skill in the art.

In another embodiment the peptides are employed in a suitable competitive assay method with test compounds to assess the ability of the test compound to competitively displace the peptide from binding to its presently unknown receptor on the pathogen. Where desired, and depending on the assay selected, a microorganism (e.g., bacterium, virus or fungus) to which the selected peptide(s) are known to bind, e.g., *E. coli* or *K. pneumoniae* strains, may be immobilized directly or indirectly on a suitable surface, e.g., in an ELISA format. Such immobilization surfaces are well known. For example, an inert bead may be used. Further, the ligand may be bound to a 96-well plate, or even other plates known by those skilled in the art. Thereafter selected amounts of the test compounds and the peptides of this invention are exposed to the immobilized microorganism and those test compounds selected which can compete with the peptides or peptide derivatives or multimers according to the present invention for binding to the immobilized microorganism. Once those test compounds, which compete with the peptides for binding to the receptor or target on or in the bacteria or fungi are identified, they may be further screened for antibacterial or anti-fungal activities (e.g. for the minimal inhibition concentration (MIC)) as described in the examples below.

In a preferred embodiment of the present invention the microorganism used in the competitive method of testing is selected from the group consisting of *Escherichia coli, Enterobacter cloacae, Erwinia amylovora, Klebsiella pneumoniae, Morganella morganii, Salmonella typhimurium, Salmonella typhi, Shigella dysenteriae, Yersinia enterocolitica, Acinetobacter calcoaceticus, Acinetobacter baumannii, Agrobacterium tumefaciens, Francisella tularensis, Legionella pneumophila, Pseudomonas syringae, Rhizobium meliloti Pseudomonas aeruginosa, Proteus vulgaris, Proteus mirabilis, Stenotrophomonas maltophilia, Haemophilus influenzae*, and *Micrococcus luteus*.

In yet a further aspect, the invention provides an isolated nucleic acid molecule comprising a nucleotide sequence encoding a peptide and/or peptide derivative and/or multimer according to the invention. The nucleic acid encodes a antimicrobial peptide and/or peptide derivative and/or multimer of the invention in operative association with a regulatory sequence directing the expression thereof in a host cell.

In yet another aspect, the invention provides a host cell transfected or comprising the above-described nucleic acid molecule.

EXAMPLES

The invention is illustrated by the following examples without being limited to these:

Example 1

Peptide Synthesis

Peptides were synthesized on Rink amide MBHA resin or Wang resin (MultiSynTech GmbH, Witten, Germany) with standard 9-fluorenylmethoxycarbonyl/tert-butyl (Fmoc/ᵗBu)-chemistry using a 25 µmol-scale on the multiple synthesizer SYRO2000 (MultiSynTech). Amino acid derivatives were activated in situ with di-isopropyl carbodiimide (DIC) in the presence of 1-hydroxy-benzotriazole (HOBt) (Singer D, Lehmann J, Hanisch K, Hartig W, & Hoffmann R. Neighbored phosphorylation sites as PHF-tau specific markers in Alzheimer's disease. Biochemical and Biophysical Research Communications 346: 819-28, 2006). After completion of the peptide synthesis, 5(6)-carboxyfluorescein (Fluka Chemie GmbH, Buchs, Switzerland) was coupled to the unprotected N-terminus with DIC/HOBT using a part of the resin. The unlabeled or fluorescein-labeled peptides were cleaved with trifluoroacetic acid (TFA) containing 12.5% (v:v) of a scavenger mixture (ethandithiole, m-cresole, thioanisole and water, 5:10:10:10). The peptides were precipitated with cold diethyl ether and purified by RP-HPLC using a linear aqueous acetonitrile gradient in the presence of an ion pair reagent (0.1% TFA) and a Jupiter $C_{18}$ column (21.2 mm internal diameter, 250 mm length, 15 µm particle size, 30 nm pore size) (Phenomenex Inc., Torrance, USA). The purities of the peptides were judged by RP-HPLC on a Jupiter $C_{18}$-column (4.6 mm internal diameter, 150 mm length, 5 µm particle size, 30 nm pore size; Phenomenex). The molecular weight of the peptide was confirmed by matrix-assisted laser desorption/ionisation time-of-flight mass spectrometry (MALDI-TOF-MS; 4700 proteomic analyzer; Applied Biosystems GmbH, Darmstadt, Germany).

TABLE 2

Peptide sequences of oncocin and its stabilized derivatives

| SEQ ID NO. | Synthesis number | Sequence |
|---|---|---|
| 1* | A33 B3 | VDKPPYLPRPRPPRRIYNR-NH₂ |
| 2 | A76 B2 | VDKPPYLPRPRPPROTYNO-NH₂ |
| 3 | A76 B4 | VDKPPYLPRPRP-4tHyp-R-4tHyp-TYNO-NH₂ |
| 4* | A53 F2 | VDKPPYLPRPRPPROIYNO-NH₂ |

*Reference examples

Example 2

Serum Stability Assay

The serum stabilities of all peptides were determined in pure and 25% (v/v) aqueous pooled mouse serum (PAA Laboratories GmbH, Pasching, Austria) (Hoffmann R, Vasko M, & Otvos L. Serum stability of phosphopeptides. *Analytica Chimica Acta* 352: 319-25, 1997). Peptides were dissolved in serum at a final concentration of 75 µg/mL and incubated at 37° C. Aliquots taken in triplicates after 0, 30, 60, 120 and 240 min were precipitated by addition of trichloroacetic acid to a final concentration of 3% (v/v). After 10 minutes on ice, the samples were centrifuged, the supernatant neutralized with sodium hydroxide solution (1 mol/L) and stored at −20° C. The samples were analyzed on the analytical Jupiter $C_{18}$-column using a linear aqueous acetonitrile or methanol gradient containing 0.1% (v/v) TFA. The metabolites were identified by MALDI-TOF-MS.

TABLE 3

Serum stabilities of oncocin and selected stabilized oncocin derivatives determined in full mouse serum by their half life times.

| SEQ ID NO. | Synthesis number | Sequence | Half life time |
|---|---|---|---|
| 1* | A33 B3 | VDKPPYLPRPRPPRRIYNR-NH₂ | 30 min |
| 2 | A76 B2 | VDKPPYLPRPRPPROTYNO-NH₂ | 120 min |
| 3 | A76 B4 | VDKPPYLPRPRP-4tHyp-R-4tHyp-TYNO-NH2 | >480 min (60%) |
| 4* | A53 F2 | VDKPPYLPRPRPPROIYNO-NH2 | 175 min |

*Reference examples

Oncocin (SEQ ID NO. 1) was relatively fast degraded in mouse serum with a half life time of only 30 min. Considering that the peptides need about 60 min to kill the bacteria, a systemic application would require more than four times higher peptide concentrations to treat such infections. The major metabolites identified by MALDI mass spectrometry resulted from an enzymatic cleavage between positions Arg15/Ile16 and Asn18/Arg19. These positions were stabilized by replacing arginine in positions 15 and 19 with ornithine (Orn) (SEQ ID NO. 2) and/or isoleucine in position 16 with threonine (SEQ ID NO. 2 and 3). The oncocin derivatives (SEQ ID NO. 2 and 3) intriguingly showed an increased stability in full mouse serum. An even higher stability against serum proteases was obtained by mutating four residues of the oncocin sequence, i.e. replacing Pro13 and Arg15 with 4-trans-hydroxyproline (4Hyp), Arg19 with Orn, and Ile16 with either Thr (SEQ ID NO. 3). Thus 60% of the starting derivative with SEQ ID NO. 4 were not degraded after 480 min.

Example 3

Stability Against Bacterial Proteases

Bacteria Culture

Bacteria (*E. coli* BL21 AI) were cultured over night at 37° C. in nutrient broth (Carl Roth GmbH & Co. KG, Karlsruhe, Germany). This suspension was centrifuged (5000 rpm, 4° C.) in a AVANTI® J-20-XP centrifuge using a JLA-10500 rotor (Beckman coulter, Fullerton, USA). The pellet was washed with phosphate buffered saline (PBS, 8.7 mmol/L $Na_2HPO_4$, 1.2 mmol/L $KH_2PO_4$, 150 mmol/L NaCl, pH 7.4) and centrifuged in an ALLEGRA® 21 R centrifuge (Beckman Coulter, 3000 rpm, 4° C., 20 min). The pellet was resuspended in PBS (60 mg/mL) and lysed on ice using ultra sonic (2×2 min with 2 s on/2 s off) applied via micro tip (750 W, 40% amplitude; Fisher Biobiock Scientific, Illkirch, France). One mL aliquots were centrifuged (15400 rpm, 20 min, 4° C.) and the supernatant was stored at −80'C.

Bradford Protein Assay

The peptide concentration was determined with a Bradford protein assay (Bradford M M. Rapid and Sensitive Method for Quantitation of Microgram Quantities of Protein Utilizing Principle of Protein-Dye Binding. Analytical Biochemistry 72: 248-54, 1976). Briefly, 0.01% (w/v) Coomassie brilliant blue G250 was dissolved in 5% aqueous ethanol containing 8.5% orthophosphoric (Bradford reagent). The mixture was incubated first at 60° C. for 1 h and then at room temperature for 12 h. After filtration 200 μl of the reagent were mixed with 50 μl sample solution in a polystyrole 96-well plate and incubated for 15 min in the dark. The absorption was measured at 595 nm against the negative control (50 μl PBS+200 μL Bradford reagent). The protein concentration was calculated from a calibration curve of bovine serum albumin.

Bacterial Protease Stability Assay

The stability against bacterial proteases was determined in a bacterial lysate of *E. coli* BL21 AI adjusted with PBS to a protein concentration of 0.5 mg/mL. Peptides were dissolved in the bacterial lysate at a final concentration of 150 μg/mL and incubated at 37° C. Aliquots were taken in triplicates after 0, 30, 60, 120, and 240 min and precipitated by addition of trichloroacetic acid to a final concentration of 3% (v/v). After 10 minutes on ice, the samples were centrifuged, the supernatant neutralized with sodium hydroxide solution (1 mol/L) and stored at −20° C. The samples were analyzed by RP-HPLC (Jupiter $C_{18}$-column) using a linear aqueous acetonitrile or methanol gradient containing 0.1% (v/v) TFA. Metabolites were identified by MALDI-TOF-MS.

TABLE 4

Half life times of oncocin and selected oncocin derivatives determined in lysates of *Escherichia coli* BL21 AI (protein concentration of 0.5 mg/mL).

| SEQ ID NO. | Synthesis number | Sequence | Half life time |
|---|---|---|---|
| 1* | A33 B3 | VDKPPYLPRPRPPRRIYNR-NH$_2$ | 60 min |
| 2 | A76 B2 | VDKPPYLPRPRPPROTYNO-NH$_2$ | 170 min |
| 3 | A76 B4 | VDKPPYLPRPRP-4tHyp-R-4tHyp-TYNO-NH$_2$ | 240 min |

*Reference examples

In contrast to serum proteases, the proteases present in the bacterial lysate cleaved oncocin (SEQ ID NO. 1) at three different sites, i.e. between positions Pro10/Arg11, Pro13/Arg14, and Arg15/Ile16, with a half life time of only 60 min. These cleavage sites were stabilized by substituting (i) Pro13 with 4tHyp, (ii) Arg15 with ornithine or 4tHyp, and (iii) Ile16 with Thr. Orn in position 19 was kept to stabilize the sequence against serum proteases. Both oncocin analogs (SEQ ID NO. 2 and SEQ ID NO. 3) were at least three times more stable than the original oncocin sequence. Especially the peptide according to SEQ ID NO. 3 was extremely stable. This will prevent any bacterial resistance mechanisms based on elevated expression levels of proteases.

Example 4

Antibacterial Activity

Minimal inhibitory concentrations were determined in triplicates by a liquid broth microdilution assay in sterile 96-well plates (Greiner Bio-One GmbH, Frickenhausen, Germany) using a total volume of 100 μL per well (Amsterdam, D. Susceptibility testing of antimicrobials in liquid media in *Antibiotics in laboratory medicine* (ed. Lorian, V.) 52-111 (Lippincott Williams & Wilkins, Baltimore, 1996)). Aqueous peptide solutions (1 mg/mL) were serially two-fold diluted in 1% tryptic soy broth (TSB). A typical dilution series ranged from 128 μg/mL to 0.5 μg/mL in eight steps. Overnight cultures of bacteria were diluted with 1% TSB to $1.5 \times 10^7$ cells/mL (*Klebsiella pneumoniae* DSM 681, *Escherichia coli* BL21AI and DSM 10233) and $4 \times 10^7$ cells/mL (*Micrococcus luteus* ATCC 10240). Fifty μL of these solutions were added to each well gaining a starting cell concentration of $7.5 \times 10^5$ cells/well and $2 \times 10^6$ cells/well, respectively. The plates were incubated at 37° C. and the absorbance of each well was measured after 20±2 h at 595 nm. The MIC-values were defined as the lowest peptide concentration where the absorbance value did not exceed that of the negative control (medium).

TABLE 5

Antibacterial activities of oncocin andoncocin-derivatives determined against *E. coli*, *K pneumoniae*, and *M luteus*. The minimal inhibitory concentrations (MIC) were determined in 1% TSB.

| SEQ ID NO. | Sequence | *E. coli* BL21 AI | *E. coli* DSM 10233 | *K pneumoniae* DSM 681 | *M. luteus* DSM 10240 |
|---|---|---|---|---|---|
| 1* | VDKPPYLPRPRPPRRIYNR-NH2 | 4 | 16 | 4 | 8 |
| 2 | VDKPPYLPRPRPPROTYNO-NH2 | 4 | n.d. | n.d. | 8 |

TABLE 5-continued

Antibacterial activities of oncocin andoncocin-derivatives determined against *E. coli*, *K pneumoniae*, and *M luteus*. The minimal inhibitory concentrations (MIC) were determined in 1% TSB.

| SEQ ID NO. | Sequence | E. coli BL21 AI | E. coli DSM 10233 | K pneumoniae DSM 681 | M. luteus DSM 10240 |
|---|---|---|---|---|---|
| 3 | VDKPPYLPRPRP-4tHyp-R-4tHyp-TYNO-NH2 | 4 | 2-4 | 8 | 32 |
| 4* | VDKPPYLPRPRPPROIYNO-NH2 | 8 | n.d. | n.d | 8 |

*Reference examples, n.d.: not determined

As the peptide sequence optimization aimed only at stabilizing the oncocin sequence against serum and bacterial proteases, it was very surprising to see that the antibacterial activity was also improved. This was completely unexpected as this in vitro assay does not depend on any kind of protease stability. The most stable analogue (SEQ ID NO. 3) had up to eight times improved MIC-values, i.e. 2-4 µg/mL against the two tested *E. coli* strains. At the same time the activity against *K. pneumoniae* was also improved providing now very importantly the same efficacy against both major human pathogens allowing a single dose to treat both infections.

Example 5

Cytotoxicity Assays

Cells were cultured in DMEM/Ham's F-12 medium with 5% (v:v) fetal bovine serum containing 1% (w:v) non essential amino acids and 1% (v:v) neomycin (10 mg/mL), penicillin, and streptomycin (5 mg/mL) (Invitrogen, Karlsruhe, Germany). HeLa, HEK 293, and HepG2 cells ($1\text{-}1.5\times10^4$ per well) were seeded in the same medium into 96-well plates (Greiner Bio-One GmbH), incubated overnight (37° C., 5% $CO_2$), and washed with PBS. Subsequently, the peptide solutions (100 µL per well, 600 µg/mL) were added and incubated again at identical conditions for 24 h. The cell viability was determined with the cell proliferation kit I (Roche Diagnostics GmbH; Mannheim, Germany). Briefly. 10 µL, of the methylthiazolyldiphenyl-tetrazolium bromide (MTT) reagent were added to a final concentration of 0.5 mg/mL. After incubation (4 h, 37° C., 5% $CO_2$) a sodium dodecyl sulfate (SDS) solution (10% (w:v) in 10 mmol/L hydrochloric acid, 100 µL) was added and incubated again at the same conditions for 16 h. The absorbance at 590 nm was measured on a PARADIGM™ microplate reader (Beckman Coulter, Wals, Austria) relative to a reference wavelength of 650 mm. The increased absorbance was used to estimate the viability of the cells. The positive and negative controls contained the same volumes of dimethylsuifoxide (DMSO) and PBS, respectively, instead of the peptide solution.

An important criterion to judge the pharmacological properties of antimicrobial peptides in-vitro is their toxicity against mammalian cell lines. Neither oncocin (SEQ ID NO. 1) nor its optimized analogs (SEQ ID NO. 2 and 3) showed any toxic effects on HeLa, human embryonic kidney (HEK 293), human hepatoma (HepG2) cells (FIG. 1) at peptide concentrations of 600 µg/mL, which was more than 100 fold above their MIC-values against *E. coli*.

---

The invention claimed is:

1. A peptide or peptide derivative, comprising the following general formula:

$Sub_1$-$X_1$-$D_2$-$K_3$-$P_4$-$P_5$-$Y_6$-$L_7$-$P_8$-$R_9$-$P_{10}$-$X_2$-$P_{12}$-$P_{13}$-$R_{14}$-$X_3$-$T_{16}$-$P_{17}$-$N_{18}$-$N_{19}$-$X_4$.$Sub_2$ (SEQ ID NO: 6)

wherein $Sub_1$ is the N-terminal amino group of $X_1$ or a modified N-terminal amino group of $X_1$ selected from acyl-NH— and acetyl-NH—;

wherein $X_1$ is selected from the group of residues consisting of non-polar, hydrophobic residue and residue with a positive net charge;

wherein $D_2$ is aspartic acid or glutamic acid;

wherein $K_3$, $R_9$, and $R_{14}$ are independently residues with a positive net charge;

wherein at least $P_4$, $P_5$, $P_8$, $P_{10}$, $P_{12}$, and $P_{13}$ are independently chosen from the group consisting of proline, 3,4-cis-methanoproline, 3,4-dehydroproline, homoproline, pseudoproline, and hydroxyproline;

wherein $Y_6$ is tyrosine;

wherein $L_7$ is a non-polar, hydrophobic residue;

wherein $X_2$ and $X_4$ are independently residues with a positive net charge;

wherein $X_3$ is chosen from the group consisting of residues with a positive net charge, proline, 3,4-cis-methanoproline, 3,4-dehydroproline, cis-4-hydroxyproline, trans-4-hydroxyproline (4tHyp), cis-3-hydroxyproline, trans-3-hydroxyproline, homoproline, and pseudoproline;

wherein $P_{17}$ is chosen from the group consisting of tyrosine, proline, 3,4-cis-methanoproline, 3,4-dehydroproline, homoproline, pseudoproline, and hydroxyproline;

wherein $T_{16}$ is threonine;

wherein $N_{18}$ is asparagine or glutamine;

wherein $N_{19}$ is asparagine or glutamine or $N_{19}$ is absent;

wherein $Sub_2$ is selected from the group consisting of the free C-terminal carboxyl group of $X_4$, a modified C-terminal carboxyl group of $X_4$, $X_5$ with a free C-terminal carboxyl group, $X_5$ with a modified C-terminal carboxyl group, $X_5$-$X_6$ with a free C-terminal carboxyl group, and $X_5$-$X_6$ with a modified C-terminal carboxyl group, wherein the modified C-terminal carboxyl group is $X_4$—$COR_3$ or $X_5$—$COR_3$ or $X_5X_6$—$COR_3$, wherein $R_3$ is selected from the group consisting of alkoxy, an amine, $NH_2$, an imide, lysine, hydroxylysine, ornithine, 2,4-diaminobutanoic acid, 2,3-diaminopropionic acid, 2,2'-diaminopimelic acid, desmosin, and isodesmosine;

wherein $X_5$ is selected from the group consisting of proline, 3,4-cis-methanoproline, 3,4-dehydroproline, homoproline, and pseudoproline and residues with a positive net charge; and wherein $X_6$ is selected from the group consisting of proline, 3,4-cis-methanoproline, 3,4-dehydroproline, homoproline, and pseudoproline, polar residues and hydrophobic residues;

with the proviso that when at least 6 of the residues from the group consisting of $D_2$, $P_4$, $P_5$, $P_8$, $P_{10}$, $P_{12}$, $P_{13}$, and $P_{17}$ are as defined above, the one or two remaining residues of the group consisting of $D_2$, $P_4$, $P_5$, $P_8$, $P_{10}$, $P_{12}$, $P_{13}$, and $P_{17}$ can optionally be exchanged by any other residue.

2. The peptide or peptide derivative according to claim 1, wherein $X_1$ is selected from the group of residues consisting of arginine, lysine, δ-hydroxylysine, homoarginine, 2,4-diaminobutanoic acid, β-homoarginine, D-arginine, 2-amino-3-guanidinopropionate, nitroarginine, N-methylarginine, ε-N-methyllysine, allo-hydroxylysine, 2,3-diaminopropionate, 2,2'-diaminopimelic acid, ornithine, sym-dimethylarginine, asym-dimethylarginine, 2,6-diamino-4-hexynoic acid, p-aminobenzoic acid, 3-aminotyrosine, valine, isoleucine, leucine, methionine, alanine, phenylalanine, N-methylleucine, tert-butylglycine, cyclo-hexylalanine, β-alanine, 1-aminocylcohexylcarboxylate, N-methyl-isoleucine, norleucine, norvaline and N-methylvaline.

3. The peptide or peptide derivative according to claim 1, wherein $X_2$ and $X_4$ are independently selected from the group of residues consisting of arginine, lysine, δ-hydroxylysine, homoarginine, β-homoarginine, D-arginine, 2,4-diaminobutanoic acid, 2-amino-3-guanidinopropionic acid, nitroarginine, nitrosoarginine, N-methylarginine, ε-N-methyllysine, allo-hydroxylysine, 2,3-diaminopropionate, 2,2'-diaminopimelic acid, ornithine, sym-dimethylarginine, asym-dimethylarginine, 2,6-diamino-4-hexynoic acid, and 3-aminotyrosine.

4. The peptide or peptide derivative according to claim 1, wherein $X_3$ is selected from the group of residues consisting of arginine, lysine, δ-hydroxylysine, homoarginine, β-homoarginine, D-arginine, 2,4-diaminobutanoic acid, 2-amino-3-guanidinopropionic acid, nitroarginine, nitrosoarginine, N-methylarginine, ε-N-methyllysine, allohydroxylysine, 2,3-diaminopropionate, 2,2'-diaminopimelic acid, ornithine, sym-dimethylarginine, asym-dimethylarginine, 2,6-diamino-4-hexynoic acid, 3-aminotyrosine.

5. The peptide or peptide derivative according to claim 1, wherein $K_3$ is selected from the group of residues consisting of histidine, lysine, arginine, homoarginine, and ornithine.

6. The peptide or peptide derivative according to claim 1, wherein $L_7$ is selected from the group of residues consisting of leucine, isoleucine, valine, and tert-butylglycine.

7. The peptide or peptide derivative according to claim 1, wherein $Sub_2$ is a modified C-terminus of $X_4$ consisting of —$NH_2$.

8. The peptide or peptide derivative according to claim 1, wherein at least one peptide bond of the peptide backbone is a modified peptide bond selected from the group consisting of a reduced amide bond, an alkylated amide bond, and a thioamide bond.

9. The peptide or peptide derivative according to claim 1, wherein the peptide or peptide derivative at its N-terminus is linked to a further peptide.

10. A multimer comprising at least one peptide or peptide derivative according to claim 1.

11. A pharmaceutical composition comprising the peptide or peptide derivative according to claim 1.

12. A pharmaceutical composition comprising the multimer according to claim 10.

13. The peptide or peptide derivative according to claim 1, comprising the sequence VDKPPYLPRPRPPROTYNO-$NH_2$ (SEQ ID NO:2).

14. The peptide or peptide derivative according to claim 1, comprising the sequence VDKPPYLPRPRP-4tHyp-TYNO-$NH_2$ (SEQ ID NO 3).

* * * * *